United States Patent
Crea

(10) Patent No.: US 7,713,569 B2
(45) Date of Patent: *May 11, 2010

(54) HYDROXYTYROSOL-RICH COMPOSITION FROM OLIVE VEGETATION WATER AND METHOD OF USE THEREOF

(75) Inventor: Roberto Crea, San Mateo, CA (US)

(73) Assignee: Creagri, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/190,043

(22) Filed: Jul. 5, 2002

(65) Prior Publication Data

US 2003/0108651 A1 Jun. 12, 2003

Related U.S. Application Data

(63) Continuation-in-part of application No. 09/944,744, filed on Aug. 31, 2001, now Pat. No. 6,416,808.

(60) Provisional application No. 60/356,847, filed on Feb. 13, 2002, provisional application No. 60/230,535, filed on Sep. 1, 2000.

(51) Int. Cl.
*A23D 7/00* (2006.01)

(52) U.S. Cl. .................. 426/601; 424/769; 514/27; 514/738

(58) Field of Classification Search .............. 514/27, 514/738; 426/601, 658, 430, 431, 417, 425, 426/427, 428; 424/769
See application file for complete search history.

(56) References Cited

U.S. PATENT DOCUMENTS

| | | | |
|---|---|---|---|
| 4,370,274 A | 1/1983 | Finch et al. | |
| 4,452,744 A | 6/1984 | Finch et al. | |
| 4,522,119 A | 6/1985 | Finch et al. | |
| 5,714,150 A | 2/1998 | Nachman | |
| 5,719,129 A | 2/1998 | Andary et al. | |
| 5,998,641 A | 12/1999 | Ganguli et al. | |
| 6,117,844 A | 9/2000 | Fredrickson | |
| 6,162,480 A | 12/2000 | van Buuren et al. | |
| 6,165,475 A * | 12/2000 | Crea et al. | 424/769 |
| 6,197,308 B1 * | 3/2001 | Crea et al. | 424/769 |
| 6,358,542 B2 | 3/2002 | Cuomo et al. | |
| 6,361,803 B1 | 3/2002 | Cuomo et al. | |
| 6,416,808 B1 * | 7/2002 | Crea | 426/601 |
| 6,437,004 B1 | 8/2002 | Perricone | |
| 6,440,465 B1 | 8/2002 | Meisner | |
| 6,682,763 B2 | 1/2004 | Kuno et al. | |
| 6,746,706 B1 | 6/2004 | Van der Boom et al. | |
| 6,849,770 B2 | 2/2005 | Guzman et al. | |
| 6,936,287 B1 | 8/2005 | Crea et al. | |
| 7,261,909 B2 | 8/2007 | Crea | |
| 2002/0004077 A1 | 1/2002 | Cuomo et al. | |
| 2002/0198415 A1 | 12/2002 | Crea | |
| 2003/0108651 A1 | 6/2003 | Crea | |
| 2003/0185921 A1 | 10/2003 | Fotinos et al. | |
| 2004/0039066 A1 | 2/2004 | Crea | |
| 2005/0103711 A1 | 5/2005 | Emmons et al. | |
| 2007/0020350 A1 | 1/2007 | Numano et al. | |

FOREIGN PATENT DOCUMENTS

| | | | |
|---|---|---|---|
| EP | 0 295 722 | | 12/1988 |
| EP | 581748 | | 2/1994 |
| EP | 0 855 908 | | 8/1998 |
| ES | 2006904 | | 5/1989 |
| IT | 1276576 | | 11/1997 |
| IT | 1278025 | | 11/1997 |
| JP | 8119825 A | | 5/1996 |
| WO | WO 97/28089 | | 8/1997 |
| WO | WO 97/47711 | | 12/1997 |
| WO | WO 00/36936 | * | 6/2000 |
| WO | WO 01/76579 A1 | | 10/2001 |
| WO | WO 02/18310 A1 | | 3/2002 |

OTHER PUBLICATIONS

Walter et al., "Preparation of antimicrobial compounds by hydrolysis of oleuropein from green olives", Abstract of Applied Microbiology, 26(5), pp. 773-776, 1973.*
Chimi, H. et al., "Peroxyl and Hydroxyl Radical Scavenging Activity of Some Natural Phenoiic Antioxidants", Abstract of Jouranal of the American Oil Chemists' Society, vol. 68, No. 5, pp. 307-312, 1991.*
Saija, A. et al., "In vitro evaluation of the antioxidant activity and biomembrane interaction of the plant phenols oleuropein and hydroxytyrosol", International Journal of Pharmaceutics 166:123-133 (1998).*
Amari, S. and Maramaldi, G., *SOFW-Journal* 125:30-32, (1999).
Fehri, B., et al., *Boll. Chim. Farmaceutico* 135:42-49, (1996).
Ibbotson, S.H., et al., *The Journal of Investigative Dermatology* pp. 933-938, (1999).
Kiritsakis, A.K., *JAOCS* 75:673-681, (1998).
Papadopoulos, G. and Boskou, D., *JAOCS* 68(9):669-671, (1991).
Papadopoulos, G., et al., *Elsevier Science Pub.* pp. 321-326, (1993).
Tsimidou, M., et al., *Food Chemistry* 45:141-144, (1992).
Visioli, F., et al., *Biochemical and Biophysical Research Communications* 247:60-64, (1998).
Aziz, N.H., et al., "Comparative antibacterial and antifungal effects of some phenolic compounds" *Microbios* 93:43-54 (1998).
Computer Abstract FSTA 97(01):J0083 Limiroli et al. "1H NMR Study of Phenolics in the Vegetation Water of Three Cultivars of Olea Europaea" Journal of Agric. & Food Chem. (1996) 44 (8) 2040-2048.

(Continued)

*Primary Examiner*—James D Anderson
(74) *Attorney, Agent, or Firm*—King & Spalding LLP; Susan J. Myers Fitch; Peter J. Dehlinger

(57) ABSTRACT

The invention provides olive-derived hydroxytyrosol. According to one aspect of the invention, vegetation water is collected from olives. Acid is added to stabilize the vegetation water and prevent fermentation. The mixture is incubated to allow oleuropein to convert to hydroxytyrosol, and then fractionated to separate hydroxytyrosol from other components. The hydroxytyrosol is useful as a therapeutic and anti-oxidant for a variety of health purposes, including for the treatment of skin damage. In addition, the hydroxytyrosol is useful as a natural anti-bacterial, anti-viral and fungicidal product for agricultural and pest control applications.

18 Claims, 8 Drawing Sheets

OTHER PUBLICATIONS

Computer Abstract FSTA 2000(01):N0049 Servili et al. "High Performance Liquid Chromatography Evaluation of Phenols in Olive Fruit, Virgin Olive Oil, Vegetation Waters, and Pomace and 1D- and 2D-Nuclear Magnetic Resonance Characterization", Jourof the Amer. Oil Chemists Soc. (1999) 76 (7).

Computer Abstract Energy 1992(16):116698 Amalfitano Recovery and Purification Treatments of Water Coming form Olive Oil Extraction Processes, "Energy Innovation and the Agro-Food Industry" Ed. Corte et al. Conference: Mar. 21-23, 1990.

de la Puerta, et al., "Inhibition of Leukocyte 5-Lipoxygenase by Phenolics from Virgin Olive Oil" *Biochemical Pharmacology* 57:445-449 (1999).

Koutsoumanis, K., et al., "Modelling the effectiveness of a natural antimicrobial on Salmonella enteritidis as a function of concentration, temperature and pH, using conductance measurements" *J. of Applied Microbiology* 84:981-987 (1998).

Tassou, C.C. and Nychas, G.J.E., "Inhibition of Salmonella enteritidis by oleuropein in broth and in a model food system" *Letters in Applied Microbiology* 20:120-124 (1995).

Tranter, H.S., et al., "The effect of the olive phenolic compound, oleuropein, on growth and enterotoxin B production by *Staphylococcus aureus*" *J. of Applied Bacteriology* 74:253-259 (1993).

Visioli, F., et al., "Free Radical-Scavenging Properties of Olive Oil Polyphenols" *Biochemical and Biophysical Research Communications* 247:60-64 (1998).

Visioli, F., et al., "Oleuropein, the Bitter Principle of Olives, Enhances Nitric Oxide Production by Mouse Macrophages" *Life Sciences* 62(6):541-546 (1998).

Visioli, F., et al.,"' Waste Waters' from Olive Oil Production are Rich in Natural Antioxidants" *Experientia*, Birkhauser Verlag 51(1):32-34 (1995).

Chimi, H., et al:, *JAOCS* 68(5):307-312, (1991).

Fleming, H.P., et al., *Applied Microbiology* 18(5):856-860, (1969).

Int'l. Search Report from PCT/US03/21111; Int'l. Filing Date: Mar. 7, 2003.

Armstrong, B.K. and Doll, R., "Environmental Factors and Cancer Incidence and Mortality in Different Countries, with Special Reference to Dietary Practices" *International Journal of Cancer*, 15:617-631 (1975).

Bartsch, H., et al., "Dietary Polyunsaturated Fatty Acids and Cancers of the Breast and Colorectum: Emerging Evidence for Their Role as Risk Modifiers", *Carcinogenesis*, 20(12):2209-2218 (1999).

Bonina, F. et al., Biofenoli Dell'ulivo, *Cosm. Technol.*, (No English translation available). 2131: 18-22 (1999).

Braga et al., "Olive Oil, Other Seasoning Fats, and the Risk of Colorectal Carcinoma", *American Cancer Society*, 82:448-453 (1998).

Bruner et al., "A Systematic Review of Adverse Effects Associated with Topical Treatments for Psoriasis", *Dermatology Online Journal*, 9(1):2, 11 pages (2003).

Capasso et al., "A Highly Convenient Synthesis of Hydroxytyrosol and its Recovery from Agricultural Waste Waters", *J. Agric. Food Chem.*, 47(4):1745-1748 (1999).

Capasso et al., "Isolation Spectroscopy and selective Phytotoxic Effects of Polyphenols From Vegetable Waste Waters", *Phytochemistry*, 31(12):4125-4128 (1992).

Chan et al., "What Causes Prostate Cancer? A Brief Summary of Epidemiology", *Seminars in Cancer Biology*, 8:263-273 (1998).

D'Amicis, A. and Farchi, S., "Olive Oil Consumption and Cancer Mortality in Italy", *Advances in Nutrition and Cancer 2* (Zappia, V., et al., Eds.) 67-72, Kluwer Academic/Plenum Publishers, New York (1999).

Deiana et al., "Inhibition of Peroxynitrite Dependent DNA Base Modification and Tyrosine Nitration by the Extra Virgin Olive Oil-Derived Antioxidant Hydroxytyrosol", *Free Radical Biology & Medicine*, 26:762-769 (1999).

Feletar et al., "Treatment of Refractory Psoriatic Arthritis with Infliximab: a 12 Month Observational Study of 16 Patients", *Ann. Rheum Dis.*, 63:156-161 (2004).

Ficarra et al. "HPLC Analysis of Oleuropein and Some Flavonoids in Leaf and Bud of *Olea Europaea* L.", *IL Farmaco*, 46(6):803-815 (1991).

Gerber et al., *Epidemiology of Diet and Cancer*, Olive Oil and Cancer, Chapter 13, pp. 263-275, edited by M.J. Hill, Ellis Horwood New York (1994).

Ho, V.C., "The Use of Ciclosporin in Psoriasis: A Clinical Review," *Br. J. Dermatology*, 150(Suppl. 67):1-10 2004.

Kobayashi et al., An Alternative Approach to Atopic Dematitis: Part 1—Case Series Presentation eCAM, 1(1):49-62 (2004).

Kohyama et al., Inhibition of Arachidonate Lipoxygenase Activities by 2-(3,4-Dihydroxyphenol)ethanol, a Phenolic Compound from Olives, *Biosci. Biotech. Biochem.*, 61(2):347-350 (1997).

Kuller et al., "Dietary Fat and Chronic Diseases: Epidemiologic Overview", *Journal of the American Dietetic Association*, 97:S9-S15 (1997).

La Vecchia et al., "Monounsaturated and other Types of Fat, and the Risk of Breast Cancer", *European Journal of Cancer Prevention*, 7:461-464 (1998).

Lebwohl et al., "Psoriasis Treatment: Traditional Therapy", *Ann. Rheum Dis*, 64(Suppl. 2):ii83-ii86 (2005).

Manna et al., "Transport Mechanism and Metabolism of Olive Oil Hydroxytyrosol in CAco-2 Cells", *FEBS Letters*, 470:341-344 (2000).

Manna et al., "Biological effects of hydroxytyrosol, a polyphenol from olive oil endowed with antioxidant activity", *Advances in Experimental Medicine and Biology*, 472:115-130 (1999).

Marchetti et al., "Treatments for Mild-To-Moderate Recalcitrant Plaque Psoriasis: Expected Clinical and Economic Outcomes for First-Line and Second-Line Care", *Dermatology Online Journal*, 11(1):1, 11 pages (2005).

Martin-Moreno et al., "Dietary Fat, Olive Oil Intake and Breast Cancer Risk" *Int. J. Cancer*, 58:774-780 (1994).

Mason and Krueger, "Thioguanine for Refractory Psoriasis: A 4-Year Experience", *J. Am. Acad. Dermatol.*, 44(6):67-72 (2001).

Mattson, F.H. and Grundy, S.M., "Comparison of Effects of Dietary Saturated, Mono-unsaturated, and Poly-unsaturated Fatty Acids on Plasma Lipids and Lipoproteins in Man", *J. Lipid Res.*, 26:194-202 (1985).

Owen, R.W., et al., "The Identification of Lignans As Major Components of the Phenolic Fraction of Olive Oil" *J. Can. Res. Clin. Onc.*, 125:S31 (Abstract K22) (2000).

Owen, R.W., et al., "The Antioxidant/Anticancer Potential of Phenolic Compounds Isolated From Olive Oil", *European Journal of Cancer*, 36:1235-1247 (2000).

Owen, R.W., et al., "Phenolic Compounds and Squalene in Olive Oils: The Concentration and Antioxidant Potential of Total Phenols, Simple Phenols, Secoiridoids, Lignans and Squalene", *Food Chemical Toxicology*, 38:647-659 (2000).

Owen et al., "Olive-oil consumption and health: the possible role of antioxidants", *Lancet Oncology*, 1(2):107-112 (2000).

Pacific Health Services, Olive leaf Extract Product Information (2006).

Parthasarathy, S., et al., "Low Density Lipoprotein Rich in Oleic Acid is Protected Against Oxidative Modification: Implications for Dietary Prevention of Atherosclerosis", *Proc. Natl. Acad. Sci. USA*, 87:3894-3898 (1990).

Petroni, A., et al., "Inhibition of Platelet Aggregation and Eicosanoid Production by Phenolic Components of Olive Oil", *Thrombosis Research*, 78(2):151-160 (1995).

Rifai et al., "Inflammatory Markers and Coronary Heart Disease", *Curr. Opin. Lipidol.*, 13:383-389 (2002).

Risch, H.A., et al., "Dietary Fat Intake and Risk of Epithelial Ovarian Cancer", *Journal of the National Cancer Institute*, 86:1409-1415 (1994).

Psoriasis, $2^{nd}$ Ed., Roenigk and Maibach eds. $2^{nd}$ ed. New York Marcel Dekker, 213-214 (1991).

Romani, A., et al., Polyphenolic Content in Five Tuscany Cultivars of *Olea europaea* L., *J. Agric. Food Chem.*, 47:964-967 (1999).

Saija and Uccella, "Olive Biophenols: Functional Effects on Human Wellbeing", *Trends in Food Science & Technology*, 11(9-10):357-363 (2001).

Tuck et al., "Major Phenolic Compounds in Olive Oil: Metabolism and Health Effects", *Journal of Nutritional Biochemistry*, 13:636-644 (2002).

Tsimidou, M., et al., "Determination of Phenolic Compounds in Virgin Olive Oil by reversed-Phase HPLC with Emphasis on UV Detection", *Food Chemistry*, 44:53-60 (1992).

Visioli et al.. Olive Oils Rich in Natural Catecholic Phenols Decrease Isoprostane Excretion in Humans, *Biochemical and Biophysical Research Communications*, 278(3):797-799 (2000).

Official Action dated Oct. 28, 2009 from JP Patent Application No. 2004-519909 based on PCT/US2003/021111.

* cited by examiner

HYDROXYTYROSOL-RICH COMPOSITION FROM OLIVE VEGETATION WATER AND METHOD OF USE THEREOF

This application claims priority benefit to U.S. provisional application No. 60/356,847, filed Feb. 13, 2002, which is incorporated herein in its entirety. The present application is also a continuation-in-part of U.S. patent application Ser. No. 09/944,744, filed Aug. 31, 2001, now U.S. Pat. No. 6,416,808 which claims priority to U.S. provisional application No. 60/230,535, filed Sep. 1, 2000, both of which are incorporated herein in their entireties by reference. The corresponding PCT application number PCT/US01/27132 is also incorporated herein by reference.

FIELD OF THE INVENTION

This invention relates to a phenolic fraction of a group of compounds present in the fruit and leaves of olive plants which are known as polyphenols. Particularly, the invention provides an olive extract containing hydroxytyrosol (3,4-dihydroxyphenylethanol), with low amounts or substantially free of oleuropein and tryosol, and a method of obtaining the same and to methods of use of such compounds.

REFERENCES

Armstrong, B. K. and Doll, R., *International. J. Cancer* 15:617-631 (1975).

Bartsch, H., et al., *Carcinogenesis* 20:2209-2218 (1999).

Braga, C., et al., *Cancer* 82:448-453 (1998).

Chan, J. M., et al., *Seminars in Cancer Biology* 8:263-273 (1998).

d'Amicis, A. and Farchi, S., in: Advances in Nutrition and Cancer 2 (Zappia, V., et al., Eds.) 67-72, Kluwer Academic/Plenum Publishers, New York (1999).

Deiana, M., et al., *Free Radic. Biol. Med.* 26:762-769 (1999).

de la Puerta, R., et al., *Biochem. Pharmacol.* 57:445-449 (1999).

Ficarra, P., et al., *Farmaco* 46:803-815 (1991).

Gerber, M., *Epidemiology of Diet and Cancer*, ed. M. J. Hill, 263-275 (1994).

Kohyama, N., et al., *Biosci. Biotechnol. Biochem.* 61:347-350 (1997).

Kuller, L. H., *Journal of the American Dietetic Association* 97:S9-S15 (1997).

La Vecchia, C., et al., *European Journal of Cancer Prevention* 7:461-464 (1998).

Manna, C., et al., *FEBS Letters* 470:341-344 (2000).

Martin-Moreno, J. M., et al., *Int. J. Cancer* 58:774-780 (1994).

Mattson, F. H. and Grundy, S. M., *J. Lipid Res.* 26:194-202 (1985).

Owen, R. W., et al., *J. Can. Res. Clin. Onc.* 125:S31 (2000a).

Owen, R. W., et al., *Eur. J. Cancer* 36:1235-1247 (2000b).

Owen, R. W., et al., *Food Chem. Toxic.* 38:647-659 (2000c).

Parthasarathy, S., et al., *Proc. Natl. Acad. Sci. USA* 87:3894-3898 (1990).

Petroni, A., et al., *Thromb. Res.* 78:151-160 (1995).

Risch, H. A., et al., *Journal of the National Cancer Institute* 86:1409-1415 (1994).

Romani, A., et al., *J. Agric. Food Chem.* 47:964-967 (1999).

Tsimidou, M., et al., *Food Chem.* 44:53-60 (1992).

Visioli, F., et al., *FEBS Letters* 468:159-160 (2000).

Visioli, F. and Galli, C., *Nutr. Rev.* 56:142-147 (1998).

BACKGROUND OF THE INVENTION

A high amount of dietary fat has been implicated in the development of several diseases (Owen et al., 2000c). Atherosclerosis (Kuller, 1997) and coronary heart disease (Gerber, 1994), as well as cancer of the breast (La Vecchia et al., 1998), prostate (Chan et al., 1998), ovary (Risch et al., 1994), and colon (Armstrong and Doll, 1975) have each been associated with elevated dietary fat. However, evidence indicates that it is not only the amount, but also the type of dietary fat that is important in the etiology of some cancers (Bartsch et al., 1999).

Olive oil, the principal fat component of the Mediterranean diet, has been associated with a lower incidence of coronary heart disease (Owen et al., 2000b; Parthasarathy et al., 1990; Mattson and Grundy, 1985) and certain cancers (d'Amicis and Farchi, 1999; Braga et al., 1998; Martin-Moreno et al., 1994). Several laboratories have reported that the hydrolysis of the olive oil phenolics oleuropin and other family members lead to small phenolic components with strong chemoprotective activity (Owen et al., 2000a; Manna et al., 2000). In particular, the olive oil phenolic hydroxytyrosol prevents low density lipoprotein (LDL) oxidation (Visioli and Galli, 1998), platelet aggregation (Petroni et al., 1995), and inhibits 5- and 12-lipoxygenases (de la Puerta et al., 1999; Kohyama et al., 1997). Hydroxytyrosol has also been found to exert an inhibitory effect on peroxynitrite dependent DNA base modification and tyrosine nitration (Deiana et al., 1999), and it counteracts cytotoxicity induced by reactive oxygen species in various human cellular systems (Manna et al., 2000). Finally, studies have shown that hydroxytyrosol is dose-dependently absorbed in humans following ingestion, indicating its bioavailability (Visioli et al., 2000).

Conventionally, olive oil production involves crushing olives, including the pits, to produce a thick paste. During this procedure, the crushed olives are continuously washed with water, a process known as "malaxation." The paste is then mechanically pressed to squeeze out the oil content. In addition to providing olive oil, the pressing also squeezes out the paste's water content. Such washing and pressing steps yield a considerable amount of water, referred to as "vegetation water."

Both the pit and the pulp of olives are rich in water-soluble, phenolic compounds. Such compounds are extracted from olives during malaxation, according to their partition coefficients, and end up in the vegetation water. This explains why various phenolic compounds, such as oleuropein and its derivatives, produced in olive pulp, can be found in abundance in vegetation waters. Similarly, a number of monophenolic compounds, such as tyrosol and its derivatives, produced in olive pits, are also abundant in vegetation waters.

Because of the strong chemoprotective activity of hydroxytyrosol, it is desirable to develop a method which produces an aqueous olive extract with a high percentage of hydroxytyrosol.

SUMMARY OF THE INVENTION

In one aspect, the invention includes a method of producing a hydroxytyrosol-rich composition. The method has the steps of (a) producing vegetation water from olives, preferably from the meat (or pulp) of depitted olives, (b) adding acid to the vegetation water, preferably, in an amount to produce a pH between 1 and 5, and more preferably between 2 and 4, and (c) incubating the acidified vegetation water until at least 50%, preferably at least 75%, and more preferably at least 90% of the oleuropein originally present in the vegetation water has been converted to hydroxytyrosol. In a preferred embodiment, the acidified vegetation water is incubated for a period of at least two months, and even more preferably, the acidified vegetation water is incubated up to a period of approximately between 6-12 months.

In one embodiment, the incubating is carried out until the vegetation water has a weight ratio of hydroxytyrosol to oleuropein of between 1:1 and 200:1, preferably 4:1 and 200:1, and more preferably 10:1 and 100:1. In a related embodiment, the incubating is carried out until the vegetation water has a weight ratio of hydroxytyrosol and tyrosol of between 3:1 and 50:1, typically 5:1 to 30:1.

The method may further include fractionating the incubated, vegetation water to separate hydroxytyrosol from other components, and/or drying the vegetation water rich in hydroxytyrosol to produce a dried extract. In one embodiment, the incubated vegetation water is extracted with an organic solvent to produce a 20%, or preferably 95% or more rich fraction in hydroxytyrosol.

Also provided is an injectable composition that includes a hydroxytyrosol-rich composition prepared by one or more of the embodiments described above.

In another aspect, the invention includes a method of producing a hydroxytyrosol-rich composition that includes the steps of (a) producing vegetation water from olives; (b) hydrolyzing the oleuropein and other large phenolic molecules by addition of acid (c) optionally, drying the vegetation water; (d) contacting the optionally dried vegetation water with a supercritical fluid; and (e) recovering the hydroxytyrosol-rich composition from the contacted vegetation water. In one embodiment, the hydroxytyrosol-rich composition includes at least about 95 percent by weight hydroxytyrosol. In another embodiment, the hydroxytyrosol-rich composition includes at least about 97 percent by weight hydroxytyrosol. In yet another embodiment, the hydroxytyrosol-rich composition includes at least about 99 percent by weight hydroxytyrosol.

In another aspect, a method of producing a hydroxytyrosol-rich composition that includes the steps of (a) producing vegetation water from olives; (b) hydrolyzing the oleuropein and other large phenolic molecules by addition of acid (c) optionally, drying the vegetation water; (d) extracting the vegetation water with a suitable organic solvent, such as Ethyl Acetate (EtAc); and (e) recovering a fraction that contains hydroxytyrosol in a purity equal or higher than 95% of the total phenolic fraction. In one embodiment, the hydroxytyrosol-rich composition includes at least 20% of a phenolic fraction containing about 95 percent by weight hydroxytyrosol. In one embodiment, the EtAc fraction is purified by silica gel chromatography or other gel chromatography to obtain an hydroxytyrosol fraction containing 95% or more by weight hydroxytyrosol.

In one embodiment, the recovering step described above includes the steps of (a) recovering the supercritical fluid, where the supercritical fluid contains the hydroxytyrosol; and (b) vaporizing the supercritical fluid to extract the hydroxytyrosol-rich composition. In another embodiment, the contacting step described above comprises the steps of (a) providing a porous membrane having opposite sides in a module under pressure with the membrane serving as a barrier interface between a fluid and a dense gas, the membrane being nonselective for said hydroxytyrosol; (b) providing the supercritical fluid into the module on one side of the membrane and the vegetation water on the opposite side of the membrane; (c) and extracting the hydroxytyrosol across the membrane as driven by a concentration gradient of the hydroxytyrosol between the vegetation water and the supercritical fluid. In one embodiment, the porous membrane is a hollow fiber membrane. In another embodiment, the supercritical fluid is carbon dioxide.

In another embodiment, the present invention comprises a method of producing a hydroxytyrosol-rich composition that includes the steps of (a) producing vegetation water from olives; (b) hydrolyzing the oleuropein and other large phenolic molecules by addition of acid; and (c) spray drying, i.e., evaporating the acidified vegetation water thereby resulting in a powder containing hydroxytyrosol. In another embodiment, the evaporation step described above is performed by the addition of maltodextrins to the acidified vegetation water to preferably result in a powder containing approximately 1 to 5% hydroxytyrosol, and more preferably, a powder containing approximately 2% hydroxytyrosol.

In another aspect, the invention includes a dietary supplement comprising an aqueous extract of olives containing a weight ratio of hydroxytyrosol to oleuropein of between 4:1 and 200:1, typically 10:1 and 100:1.

In a related aspect the invention includes a dietary supplement comprising an aqueous extract of olives containing a weight ratio of hydroxytyrosol and tyrosol of between 3:1 and 50:1, typically 5:1 and 30:1.

The above supplements may be dried, preferably by spray drying, to provide a powder extract, which can formulated into a tablet, capsule, pill, or confection food additive. Alternatively, the above supplements may be incorporated in a pharmaceutical formulations such as into a hydroxytyrol-rich injectable formulation.

Also provided are methods of protecting skin against adverse effects of exposure to ultraviolet radiation (UVR) comprising administering to a subject in need of such protection a pharmaceutically effective amount of a treatment agent having a weight ratio of hydroxytyrosol to oleuropein of between about 1:1 and about 200:1, preferably between about 4:1 and about 100:1, and more preferably between about 10:1 and about 50:1. The agent may also include a sunscreen for topical applications. In one embodiment, the agent is administered topically. Preferably, the agent is administered orally.

These and other aspects and features of the invention will be more fully appreciated when the following detailed description of the invention is read in conjunction with the accompanying figures and tables.

DETAILED DESCRIPTION OF THE INVENTION

All publications, patents, patent applications or other references cited in this application are herein incorporated by reference in their entirety as if each individual publication, patent, patent application or reference are specifically and individually indicated to be incorporated by reference.

I. Definitions

Unless otherwise indicated, all terms used herein have the same meaning as they would to one skilled in the art of the present invention. It is to be understood that this invention is not limited to the particular methodology, protocols, and reagents described, as these may vary.

Figure 1:
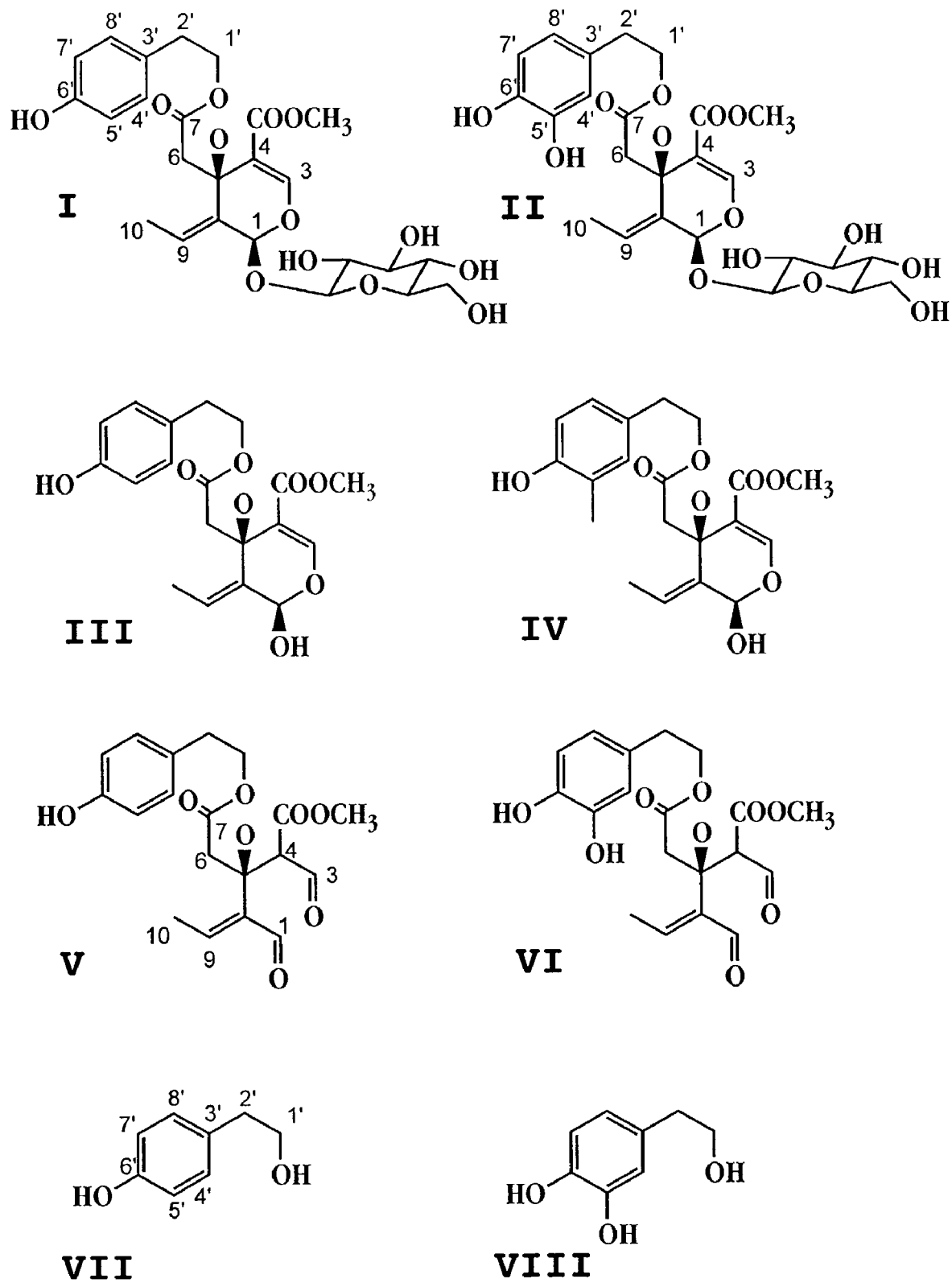
FIG. 1 shows the structures of phenolic compounds and their precursors detected in olive oil: ligstroside (I); oleuropein glucoside (II); aglycone of ligstroside (III); aglycone of oleuropein glucoside (IV); dialdehydic form of ligstroside aglycone lacking a carboxymethyl group (V); dialdehydic form of oleuropein glucoside aglycone lacking a carboxymethyl group (VI); tyrosol (VII); hydroxytyrosol (VIII).

By "oleuropein" is intended secoiridoid glucoside oleuropein (Structure II in FIG. 1).

By "tyrosol" is intended 4-hydroxyphenethyl alcohol (Structure VII in FIG. 1).

By "hydroxytyrosol" is intended 3, 4-dihydroxyphenethyl alcohol (Structure VIII in the FIG. 1).

II. Method of the Invention

The invention provides, in one aspect, provides a hydroxytyrosol-rich composition from olive-derived vegetation water. It has been discovered that under specific conditions, as described below, hydroxytyrosol may be obtained from the vegetation water of olives. Considered below are the steps in practicing the invention.

A. Producing Vegetation Water

The method of the invention employs olives that may be obtained from conventional and commercially available sources such as growers. Preferably, the vegetation water is obtained from pitted olives. The olives processed according to the method disclosed herein may be pitted by any suitable means. Pits in the olives contain tyrosol which is an undesired component in the vegetation water and which may not be appreciably broken down by the acid treatment described below. The pits may be separated from the pulp manually or in an automated manner as described below. Preferably, such means should be capable of segregating the pits without breaking them, which might otherwise cause higher concentrations of tyrosol in the vegetation water. In another embodiment, hydroxytyrosol is extracted from vegetation water obtained from olives that have not been pitted.

To produce vegetation water, olive pulp from the olives is first pressed to obtain a liquid-phase mixture including olive oil, vegetation water, and solid by-products. Thereafter, the vegetation water is separated from the rest of the liquid phase mixture and collected. Exemplary methods of obtaining vegetation water are described in co-owned U.S. Patent Application Nos. 6,165,475 and 6,197,308, both to R. Crea, each of which are expressly incorporated herein by reference in their entirety.

For purposes of commercial production, it may be desirable to automate various aspects of the invention. In this regard, one embodiment contemplates the use of an apparatus as disclosed in U.S. Pat. Nos. 4,452,744, 4,522,119 and 4,370,274, each to Finch et al., and each expressly incorporated herein by reference. Briefly, Finch et al. teach an apparatus for recovering olive oil from olives. Initially, olives are fed to a pulper that separates the olive pits from the olives to obtain a pitless olive meat. The meat is then taken up by an extraction screw that subjects the meat to an extraction pressure sufficient to withdraw a liquid phase, comprising oil, water and a minor proportion of olive pulp. The liquid phase is collected in a bin and then sent to a clarifying centrifuge that separates the pulp from the liquid phase to obtain a mixture comprising olive oil and vegetation water. A purifying centrifuge then separates the vegetation water and a small proportion of solid matter from the mixture to obtain an olive oil, substantially free of vegetation water, that is collected in a tank. According to Finch et al., the water is put to a disposal means such as a sewer. The present invention, in sharp contrast, provides for the collection, saving and use of the vegetation water to extract hydroxytyrosol.

Additional devices that may be used in practicing the present invention are disclosed in Italian Patent Nos. 1276576 and 1278025, each of which is expressly incorporated herein by reference. As above, these devices can be used to separate the pulp from the pits prior to processing of the crushed olive pulp into oil, water, and solid residues.

B. Conversion of Oleuropein to Hydroxytyrosol

In one aspect of the invention, the oleuropein contained in the vegetation water is converted to hydroxytyrosol. The pH of the vegetation water may be decreased by the addition of acid, and the vegetation water allowed to incubate under conditions which, according to the discovery of the invention, promote acid hydrolysis of oleuropein to hydroxytyrosol. The sample may then be fractionated or extracted to separate hydroxytyrosol from other compounds.

In a preferred embodiment, the added acid is citric acid. The acid is added to the vegetation water, preferably to adjust the pH to 1-5, and more preferably, to a pH of 2-4. Solid citric acid can be added while continuously stirring in an amount of preferably about 25 to 50 pounds of acid per about 1000 gallons of vegetation water. The pH of the resulting solution can be monitored, and further addition of acid may be necessary to achieve the desired pH. Exemplary methods showing the conversion of oleuropein to hydroxytyrosol following the addition of citric acid are given in Examples 1 and 2.

The acid may also be an organic or inorganic acid other than citric acid. Exemplary acids which may be used in the present invention include the inorganic substances known as the mineral acids—sulfuric, nitric, hydrochloric, and phosphoric acids—and the organic compounds belonging to the carboxylic acid, sulfonic acid, and phenol (benzyl) groups. The addition of acid to the vegetation water serves several purposes: (i) it stabilizes the vegetation water from air (oxygen) polymerization of phenolic molecules; (ii) it prevents fermentation of the vegetation water by endogenous and/or exogenous bacteria and yeast; and (iii) it provides for the hydrolysis of oleuropein and other large phenolic molecules containing hydroxytyrosol, converting them into hydroxytyrosol, as shown in Examples 1 and 2. Tables 1 and 2, in Examples 1 and 2, respectively, contain data from two samples of vegetation water and the respective percent composition of various components in the samples over time following the addition of citric acid. In one embodiment, the mixture is allowed to incubate until hydroxytyrosol is 75-90% of the total combination of oleuropein and hydroxytyrosol. In another embodiment, substantially none of the oleuropein in the original mixture remains.

C. Purification of Hydroxytyrosol

Following the conversion of oleuropein to hydroxytyrosol, preferably by acid addition, the incubated vegetation water may be fractionated by a number of methods known in the art. Exemplary methods of fractionation include partitioning with an organic solvent, such as ethyl acetate, chromatographic methods, including gel chromatography, and high pressure liquid chromatography (HPLC), or supercritical fluids.

Alternatively, vegetation water obtained as described above after acidification, provides a solution which is rich in low molecular weight polyphenols, particularly hydroxytyrosol and a small amount of tyrosol and oleuropein. The concentration of hydroxytyrosol in the processed water may range from 4-5 grams per liter to 10-15 grams per liter depending upon the degree of dilution by addition of water during the olive oil extraction. In one embodiment, the invention provides a method of extraction or purification that selectively enriches the content of hydroxytyrosol without the addition of contaminants. Thus, the major polyphenolic component, hydroxytyrosol, is isolated from other members of the polyphenolic family, impurities, suspended solids, tannins, and other molecules contained in the vegetation water. Hydroxytyrosol may therefore be produced in a purity and quantity not readily available by current synthetic or natural extraction methods.

A supercritical fluid is a gas that becomes very dense above its critical temperature and pressure. Its properties are between those of a gas and liquid, resulting in increased ability to dissolve compounds. Its relatively high density, high diffusivity, and low viscosity allow it to extract compounds faster than conventional liquid solvents. Carbon dioxide is the gas used most widely for supercritical fluid processing of foods and food ingredients because it is natural, nontoxic, non-flammable, and relatively inert and leaves no residue in the extracted product. Typical liquid extraction with supercritical carbon dioxide is usually done by dispersing one phase in the other in large contacting columns or towers, where the solute containing fluid, such as juices, flows downward by gravity, and the supercritical carbon dioxide flows upward. Mass transfer occurs at the interface between the two phases.

Alternatively, continuous extraction of liquids and suspensions can be achieved using supercritical fluids, such as carbon dioxide, and porous membranes instead of contacting columns. Instead of dispersing the phases, the liquid is fed continuously through porous polypropylene membranes configured as hollow fiber bundles or spiral wound sheets. The liquid passes through the porous membranes within a pressurized module, while supercritical carbon dioxide flows countercurrently on the other side of the membrane. The pressure in the module is essentially the same, so that the extraction is driven by the concentration gradient between the fluid and the supercritical carbon dioxide. The extract may be recovered by vaporizing the carbon dioxide for recycling. An exemplary method of extraction using supercritical carbon dioxide and porous membranes is described in U.S. Pat. No. 5,490,884, which is expressly incorporated by reference herein in its entirety.

Other supercritical fluids, instead of, or in combination with, carbon dioxide. These fluids include methane, ethane, propane, butane, isobutane, ethene, propene, hydrofluorocarbons, tetrafluoromethane, chlorodifluoromethane, carbon dioxide, dinitrogen monoxide, sulphur hexafluoride, ammonia, and methyl chloride.

Example 3 describes a small scale experiment in support of the invention, wherein hydroxytyrosol was isolated from vegetation water using supercritical carbon dioxide and porous membranes. HPLC and mass spectrometry analysis of the isolated hydroxytyrosol shows the sample to be 97-99% pure hydroxytyrosol. Thus, the invention provides a hydroxytyrosol-rich composition containing at least about 80% hydroxytyrosol, preferably at least about 90% hydroxytyrosol, more preferably at least about 95% hydroxytyrosol, even more preferably at least about 97% hydroxytyrosol, and yet, even more preferably at least about 99% hydroxytyrosol.

Prior to extraction with a supercritical fluid the vegetation water may have carriers, which are known to those of skill in the art, such as maltodextran and/or polypropylene beads, added to the solution; and/or the solution may be dried. The drying step preferably removes at least about 90%, more preferably at least about 95%, and even more preferably at least about 98% of the water from the vegetation water.

An important feature of membrane reactors is the fact that contact surface interfacial area can be added independently of fluid velocities. Accordingly, the invention contemplates a large scale unit where the surface membrane area of the membrane used for extraction is at least about 100 square yards, preferably at least about 300 square yards, and even more preferably at least about 600 square yards to allow separation of hydroxytyrosol from large volumes of vegetation water. Thus, the membrane system of the invention would, in one aspect, be able to accommodate a flow rate of between 1-20 liters per minute, preferably between 5-10 liters per minute.

Additional purification methods may also be used in accordance with the invention as mentioned above. HPLC isolation of hydroxytyrosol is described in: Ficarra et al., 1991; Romani et al., 1999; and Tsimidou, 1992, each of which is expressly incorporated by reference herein.

III. Hydroxytyrosol-Rich Dietary Supplement

It should be appreciated that hydroxytyrosol produced by the method described above may be used for a variety of applications. For example, hydroxytyrosol obtained by the method of the present invention can be used: (i) as a natural anti-bacterial, anti-viral and/or fungicidal product for agricultural and/or pest control applications, and (ii) as a therapeutic and/or an anti-oxidant for a variety of health purposes. In one exemplary embodiment, the hydroxytyrosol, is administered to a mammalian subject, such as a person desirous of one or more of the benefits associated with hydroxytyrosol.

Accordingly, provided herein are compositions and methods for the protection of skin damage resulting from exposure to ultraviolet radiation (UVR). The hydroxytyrosol obtained by the method of the invention can be administered orally or parenterally. Oral dosage forms can be in a solid or liquid form. Such dosage forms can be formulated from purified hydroxytyrosol or they can be formulated from aqueous or aqueous-alcoholic extracts. Regarding the latter, aqueous or aqueous-alcoholic (e.g., water or water-ethanol) extracts can be spray-dried to provide a dry powder that can be formulated into oral dosage forms with other pharmaceutically acceptable carriers. The aqueous or aqueous-alcoholic extracts can be formulated to contain various weight ratios of hydroxytyrosol to oleuropein of between 4:1 and 200:1, preferably between about 10:1 and about 100:1. The extracts may also be formulated to contain various weight ratios of hydroxytysol and tyrosol of between about 2:1 and about 50:1, preferably between about 5:1 and about 30:1.

Preferably, the composition is orally administered to a patient in need of protection against skin damage resulting from exposure to UVR. The solid oral dosage form compositions in accordance with this invention are prepared in a manner well known in the pharmaceutical arts, and comprise hydroxytyrosol in combination with at least one pharmaceutically acceptable carrier. In making such compositions, a hydroxytyrosol-rich composition, either in substantially pure form or as a component of a raw distillate or extract, is usually mixed, diluted or enclosed with a carrier. The carrier can be in a solid form, semi-solid or liquid material which acts as a vehicle, carrier or medium for the active ingredient. Alternatively, the carrier can be in the form of a capsule or other container to facilitate oral administration. Thus, the solid oral dosage forms for administration in accordance with the present invention can be in the form of tablets, pills, powders or soft or hard gelatin capsules.

Alternatively, the hydroxytyrosol obtained in accordance with this invention for oral administration can be in liquid form wherein the pharmaceutically acceptable carrier is water or an aqueous-alcoholic medium.

The compositions for administration in the present invention can also be formulated with other common pharmaceutically acceptable excipients, including lactose, dextrose, sucrose, sorbitol, mannitol, starches, gums, calcium silicate, microcrystalline cellulose, polyvinylpyrrolidone, methylcellulose, water, alcohol and the like. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. Further, the compositions of the present invention can be formulated so as to provide quick, sustained or delayed release of the active ingredient after administration to a subject.

Parenteral formulations for use in accordance with the present invention are prepared using standard techniques in the art. The term parenteral as used herein includes subcutaneous injections, intravenous, intramuscular, intrasternal injection, or infusion techniques. Such formulations are commonly prepared as sterile injectable solutions, using a parenterally acceptable carrier such as isotonic saline solution or as a sterile packaged powder prepared for reconstitution with sterile buffer or isotonic saline prior to administration to a subject. In one preferred embodiment the parenteral formulation is an injectible formulation which comprises between 1 and 500 mg/ml of the hydroxytyrosol rich composition of the present invention. More preferably, the injectible formulation comprises between 1 to 100 mg/ml of the hydroxytyrosol rich composition, even more preferably, between 10 to 100 mg/ml of the hydroxytyrosol rich composition, and most preferably about 10 mg/ml of the hydroxytyrosol rich composition.

From the foregoing, it can be seen how various objects and features of the invention are met. Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

The following examples illustrate methods of producing hydroxytyrosol-rich compositions in accordance with the invention. The examples are intended to illustrate, but in no way limit, the scope of the invention.

EXAMPLES

Example 1

Conversion from Oleuropein to Hydroxytyrosol Following the Addition of About 25 Pounds of Citric Acid/1000 Gallons Table 1 shows the conversion of oleuropein to hydroxytyrosol over time following the addition of about 25 pounds of citric acid per 1000 gallons of vegetation water. The percentages in Table 1 are shown as weight percentages of the total phenolic compounds in the solution. As demonstrated in Table 1, hydroxytyrosol comprises over 80% of the phenolic compounds in the solution after 12 months.

TABLE 1

Conversion from Oleuropein to Hydroxytyrosol Following the Addition of About 25 Pounds of Citric Acid/1000 Gallons

| Component | Composition at T = 2 mo. | Composition at T = 3 mo. | Composition at T = 4.5 mo. | Composition at T = 12 mo. |
|---|---|---|---|---|
| Hydroxytyrosol | 30.4% | 32% | 48.4% | 80.2% |
| Tyrosol | 2.5% | 5% | 2.2% | 3.6% |
| Oleuropein | 41% | 36.6% | 25.1% | 1.2% |
| Oleuropeinaglycone | 4.2% | 4.6% | 2.7% | 3.7% |

Example 2

Conversion from Oleuropein to Hydroxytyrosol Following the Addition of About 50 Pounds of Acid/1000 Gallons Table 2 shows the conversion of oleuropein to hydroxytyrosol over time following the addition of about 50 pounds of citric acid per 1000 gallons of vegetation water. The percentages in Table 2 are shown as weight percentages of the total phenolic compounds in the solution. Significantly, as demonstrated in Table 2, hydroxytyrosol comprises over 45% of the phenolic compounds in the solution after 2 months.

TABLE 2

Conversion from Oleuropein to Hydroxytyrosol Following the Addition of About 50 Pounds of Acid/1000 Gallons

| Component | Composition at T = 2 mo. | Composition at T = 12 mo. |
|---|---|---|
| Hydroxytyrosol | 45.7% | 78.5% |
| Tyrosol | 2.9% | 3.3% |
| Oleuropein | 28.7% | 1.5% |
| Oleuropeinaglycone | 4.1% | 3.5% |

Example 3

Extraction of Hydroxytyrosol from Vegetation Water

Figure 2:
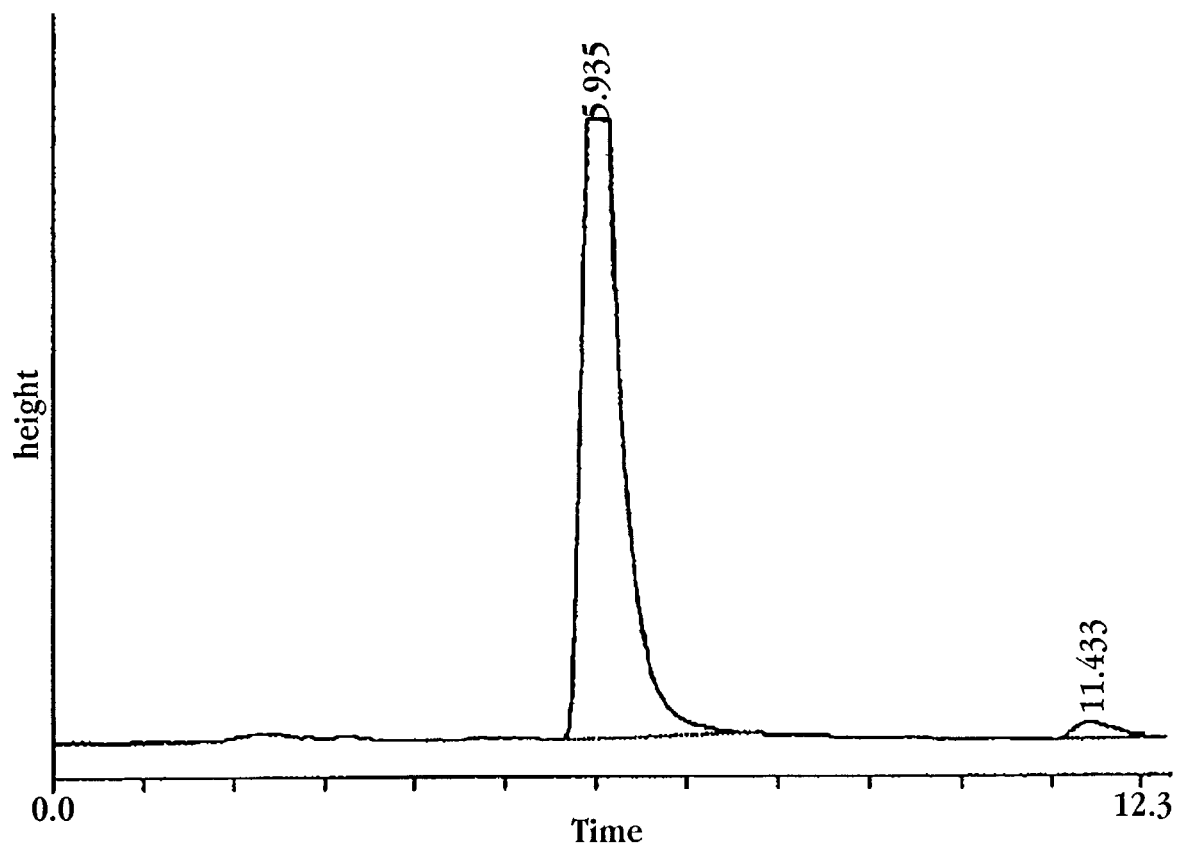
FIG. 2 shows the HPLC analysis of a hydroxytyrosol-rich composition of the invention after supercritical carbon dioxide extraction from vegetation water obtained from the meat of depitted olives.
Figure 3:
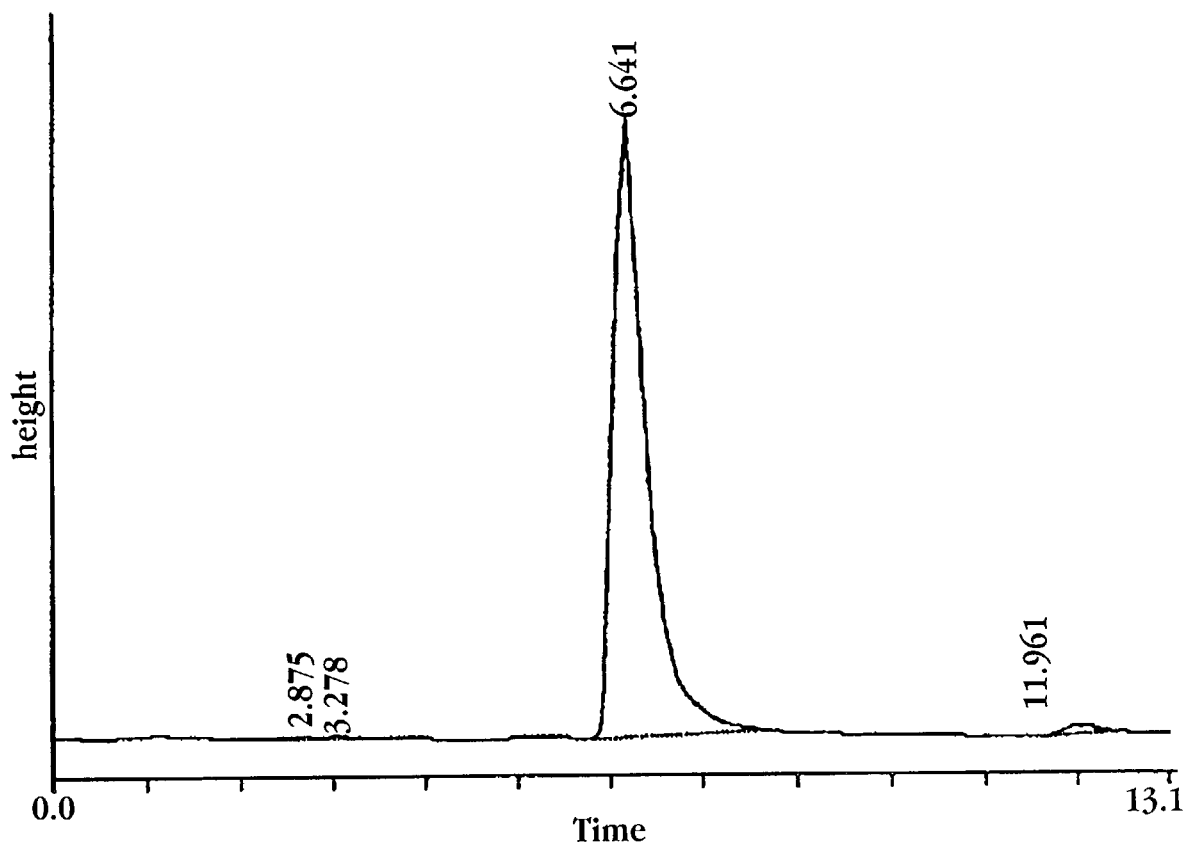
FIG. 3 shows the HPLC analysis of a hydroxytyrosol-rich composition of the invention following supercritical carbon dioxide extraction, with synthetic hydroxytyrosol.
Figure 4:
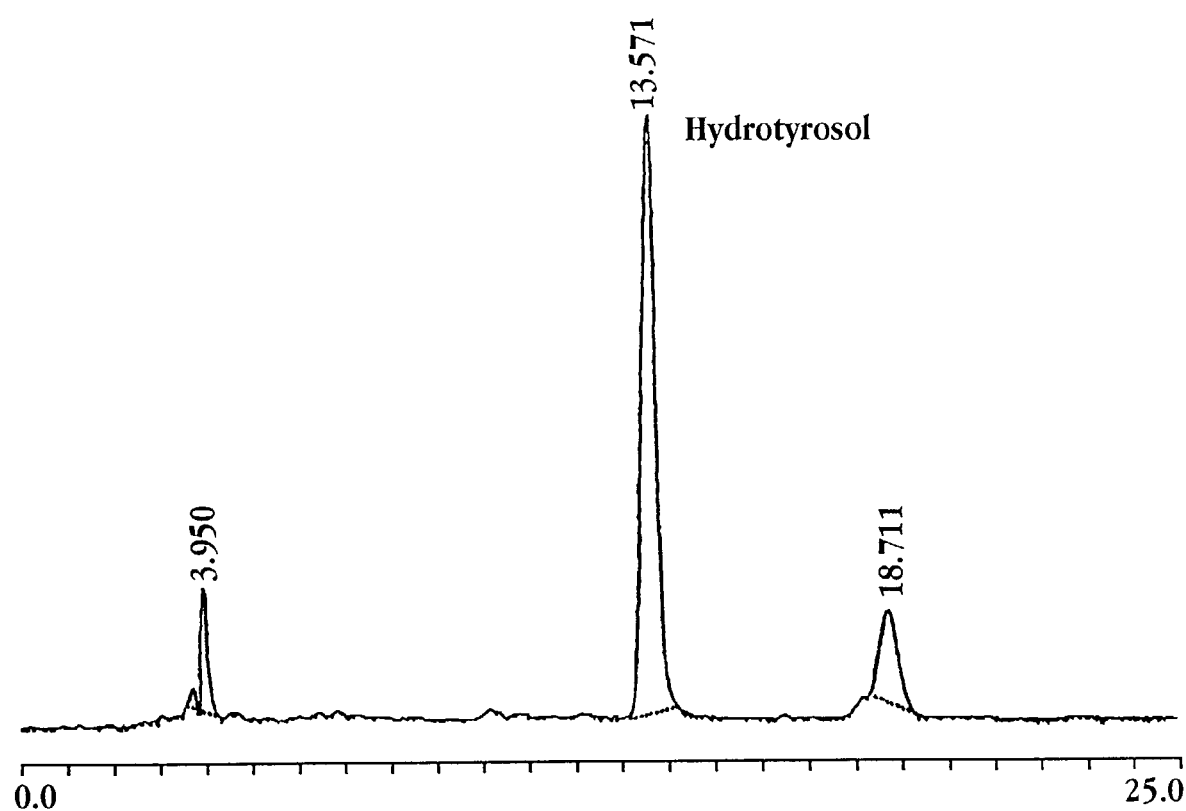
FIG. 4 shows the HPLC analysis of a hydroxytyrosol-rich composition of the invention after acidic hydrolysis of vegetation water obtained from the meat of depitted olives.

An aliquot (0.5 ml) of vegetation water containing about 40 mg of dry solid (maltodextran) was mixed with polypropylene porous beads and dried. The dry mix was used for extraction with supercritical carbon dioxide (PoroCrit, LLC, Berkeley, Calif.). The collected sample (about 2.0 mg) was analyzed by HPLC. The profile of the sample is shown in FIG. 2 and Table 3 shows the area under the major peak to be 97%. When synthetic hydroxytyrosol was added to the sample and analyzed by HPLC, one major peak appeared, as shown in FIG. 3, indicating that the major product of the sample is hydroxytyrosol (Table 4).

TABLE 3

Peak Analysis of FIG. 2 HPLC Results

| Peak No. | Time | Height (μV) | Area (μV sec) | Area (%) |
|---|---|---|---|---|
| 1 | 5.935 | 215542 | 6687705 | 97.476 |
| 2 | 11.433 | 5686 | 173104 | 2.523 |

TABLE 4

Peak Analysis of FIG. 3 HPLC Results

| Peak No. | Time | Height (μV) | Area (μV sec) | Area (%) |
|---|---|---|---|---|
| 1 | 2.875 | 1345 | 13895 | 0.26 |
| 2 | 3.278 | 1076 | 14140 | 0.265 |
| 3 | 6.641 | 211204 | 5241105 | 98.240 |
| 4 | 11.961 | 2587 | 65811 | 1.233 |

Example 4

Extraction of Hydroxytyrosol from Acidified Vegetation Water

Figure 5:
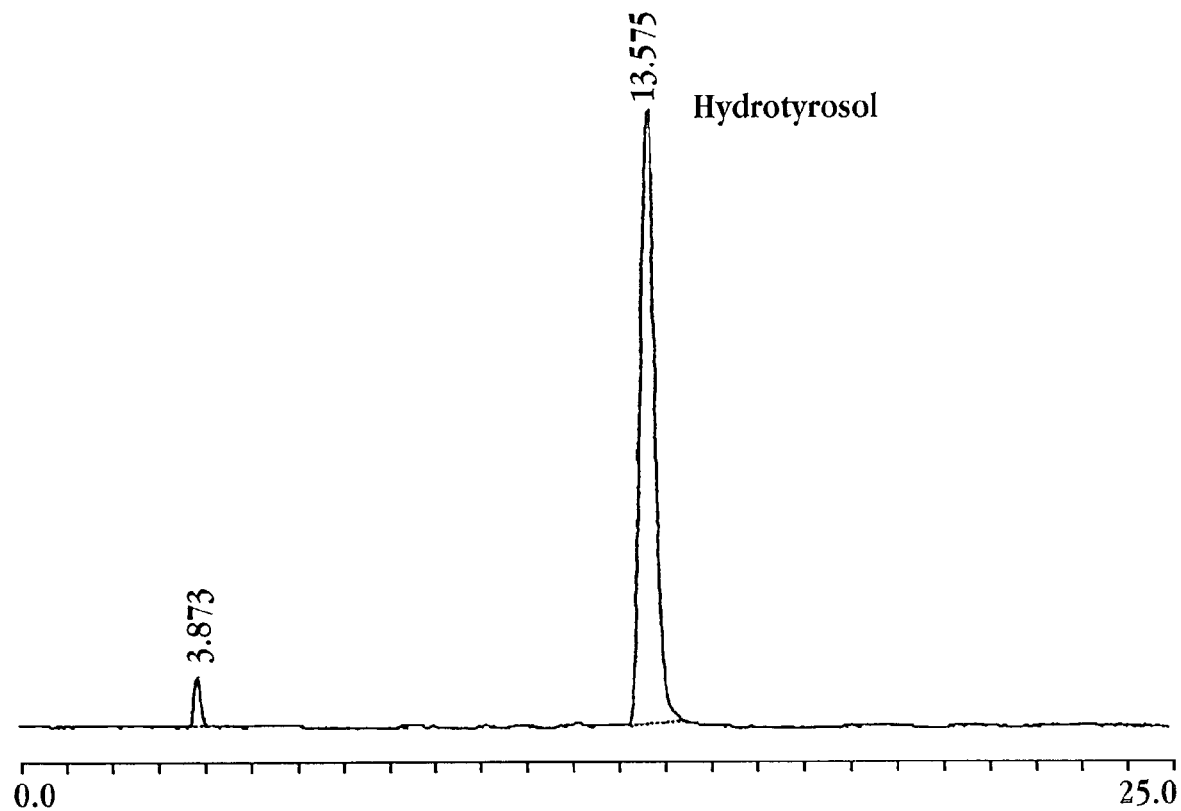
FIG. 5 shows the HPLC analysis of a hydroxytyrosol-rich composition of the invention following ethyl acetate extraction of hydroxytyrosol from vegetation water obtained from depitted olives and hydrolyzed by acid addition.

An aliquot (1 liter) of vegetation water after acidic hydrolysis was vigorously shaken with ethyl acetate in a shaking flask. The organic solvent was separated from the aqueous solution and evaporated off by rotory evaporator. The resulting thick oil (about 20 g.) was collected and analyzed by HPLC. The profile of this sample is shown in FIG. 5, and Table 5 shows the area of the major peak to be 97.457% indicating that hydroxytyrosol represents about or more than 95% of the total polyphenolic fraction in the water. Total phenolic determination by standard calorimetric assay shows that the hydroxytyrosol is contained in the oil at approximately 20% in weight.

TABLE 5

Peak Analysis of FIG. 5 HPLC Results

| Peak No. | Time | Height (μV) | Area (μV sec) | Area (%) |
|---|---|---|---|---|
| 1 | 3.873 | 7620 | 46501 | 2.542 |
| 2 | 13.575 | 95112 | 1782793 | 97.457 |

Figure 6:
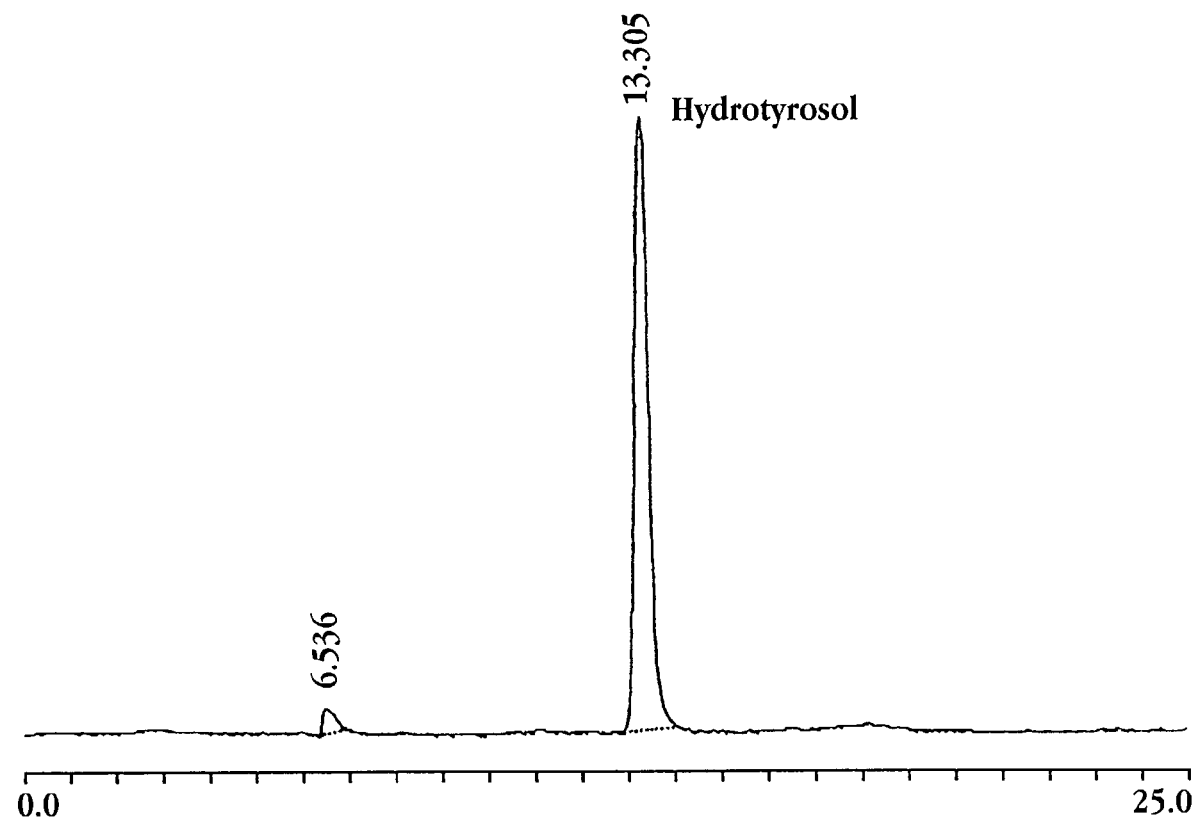
FIG. 6 shows the HPLC analysis of pure (95% or more) hydroxytyrosol obtained after purification by gel chromatography on silica gel.

This fraction was used for further purification of hydroxytyrosol by gel chromatography. Dry silica (150 g) was suspended in ethyl acetate (300 ml) to obtain a thick slurry. The slurry was poured into a glass column and the silica was allowed to stand for 15 minutes to sediment. The thick oil containing about 20% (4 g) hydroxytyrosol was dissolved in 25 ml of ethyl acetate and slowly poured over the silica gel. The purification of the hydroxytyrosol was obtained by gravity elution of the product and by the addition of ethyl acetate as the solvent. The fractions containing the pure hydroxytyrosol were collected and pooled together. The solvent was evaporated until a yellow oil was produced. As shown in FIG. 6 and in Table 6, this oil is essentially pure hydroxytyrosol (97-99%) as verified by HPLC and mass spectroscopy. The yield of this purification is about 2.8-3.0 g. Hydroxytyrosol or ca. 65%.

TABLE 6

Peak Analysis of FIG. 6 HPLC Results

| Peak No. | Time | Height (μV) | Area (μV sec) | Area (%) |
|---|---|---|---|---|
| 1 | 2.875 | 1345 | 13895 | 0.26 |
| 2 | 3.278 | 1076 | 14140 | 0.265 |
| 3 | 6.641 | 211204 | 5241105 | 98.240 |
| 4 | 11.961 | 2587 | 65811 | 1.233 |

Figure 7:
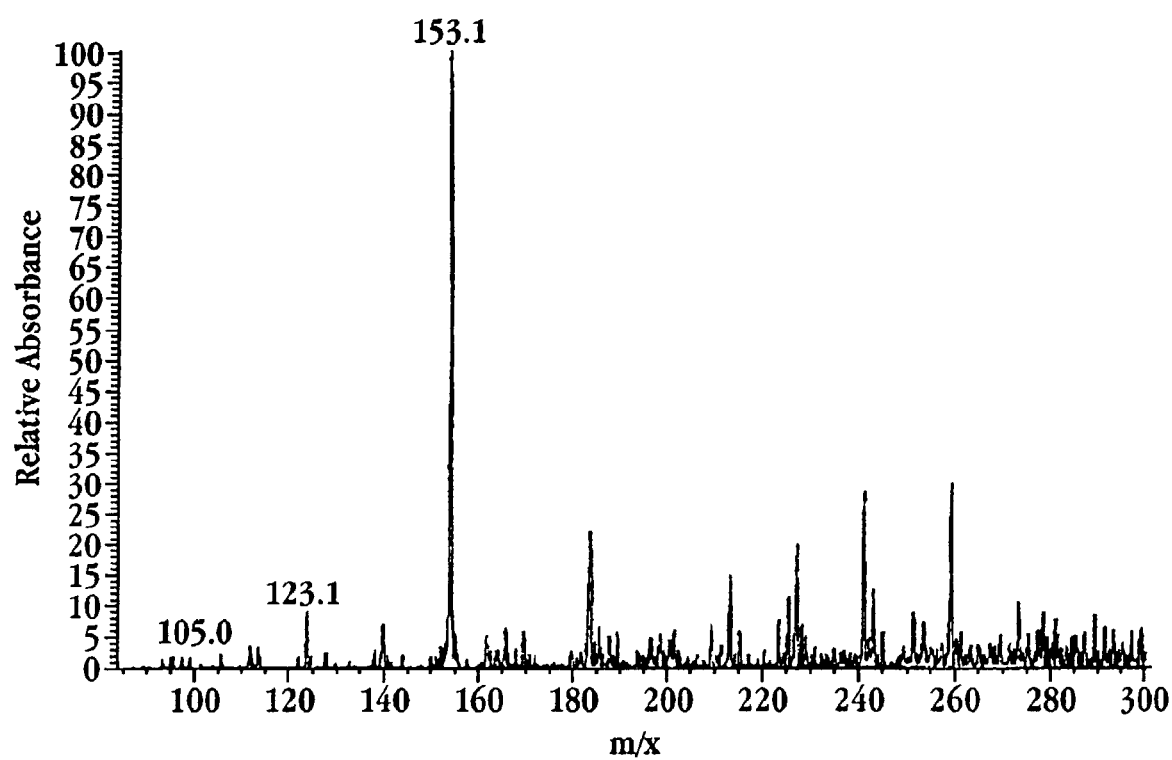
FIG. 7 shows the mass spectrum of a hydroxytyrosol-rich composition of the invention.
Figure 8:
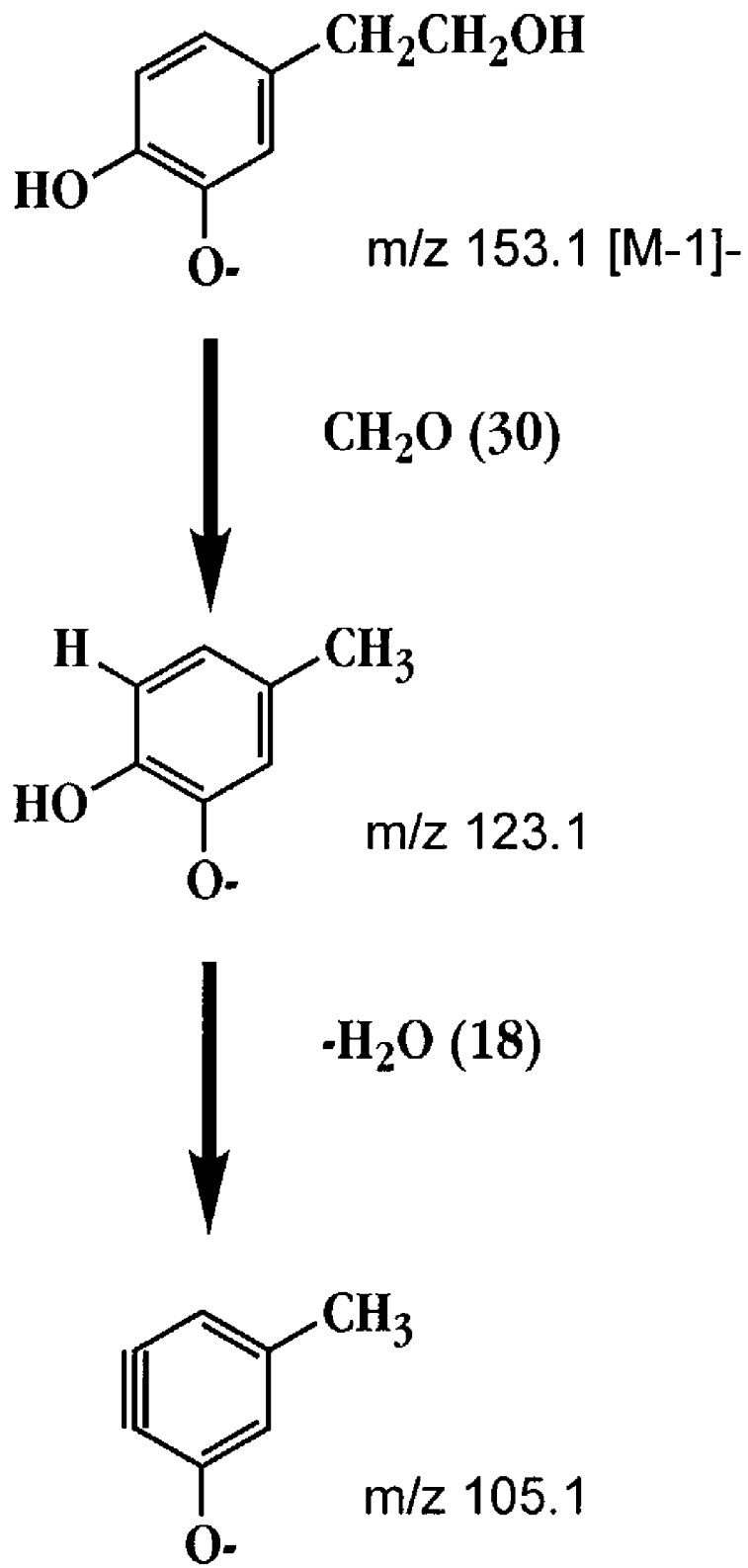
FIG. 8 illustrates the fragmentation pathway of hydroxytyrosol.

Mass spectrometry analysis of the samples obtained as described by the two procedures in Examples 3 and 4, as shown in FIG. 7, confirmed that the major product is hydroxytyrosol. The sample was diluted to a final concentration of 26 micrograms per milliliter with methanol and analyzed in negative ionization mode on a Finnigan LCQ fitted with an ESI probe. The infusion was at 3 microliters per minute using an integrated syringe pump. The temperature was 270C, needle voltage +4.2 V, sheath gas 45 units, and auxiliary gas 10 units. The fragmentation pathway of hydroxytyrosol is shown in FIG. 8. As can be seen in FIG. 7, hydroxytyrosol ( mass/charge 153.1) and its fragmentation products (123.1 and 105.1 mass/charge) account for the majority of the product abundance in the multi-stage spectrum.

Example 5

Protection Against Skin Damage from UltraViolet Radiation

Olivenol Compositions

The test article was Olivenol (Lot #1 A-1 B). Olivenol is the crude water preparation obtained by acidic hydrolysis of vegetation water (500 ml) evaporated to dryness by rotory evaporator and subsequent lyophilization. The test article vehicles were aqueous 0.5% w/v methylcellulose (oral administration) and methyl alcohol, 99.9% A.C.S. spectrophotometric grade (topical administration). Formulations were prepared once during the study and the test article was considered 75% active for the purpose of dosage calculations.

Mice

One hundred male Crl:SKH1-hrBR hairless mice (Source: Charles River Laboratories, Inc., Portage, Mich. USA) were randomly assigned to ten dosage groups (Groups 1 through 10), ten mice per group as indicated in Table 1. The body weights of male mice ranged from 17 to 28 grams.

TABLE 5

Experimental Design

| Group | Formulation and Dosage (mg/kg/day)* | Concentration (mg/mL)* | Route of Administration | Number of Male Mice | Frequency of Formulation Administration (Days) |
|---|---|---|---|---|---|
| 1 | 0 (Vehicle) | 0 (Vehicle) | Oral | 10 | 31 |
| 2 | Olivenol (1) | 0.1 | Oral | 10 | 31 |
| 3 | Olivenol (10) | 1.0 | Oral | 10 | 31 |
| 4 | Olivenol (100) | 10.0 | Oral | 10 | 31 |
| 5 | Olivenol (100) | 10.0 | Oral | 10 | 10 |
| 6 | 0 (Vehicle) | 0 (Vehicle) | Topical | 10 | 31 |
| 7 | Olivenol (1) | 0.25 | Topical | 10 | 31 |
| 8 | Olivenol (10) | 2.50 | Topical | 10 | 31 |
| 9 | Olivenol (100) | 25.00 | Topical | 10 | 31 |
| 10 | Olivenol (100) | 25.00 | Topical | 10 | 10 |

*Groups 1-5: dosage volume = 10 mL/kg.
Groups 6-10: dosages and concentrations assume a mouse body weight of 25 grams and an administration volume of 0.1 mL/mouse (i.e., 100 mcL/mouse).

Administration of Olivenol Compositions and UVR Exposure

Formulations were orally administered (via gavage) to appropriate mice once daily for either 31 (Groups 1 through 4) or 10 (Group 5) consecutive days. Formulations were topically administered (100 mcL/mouse) to appropriate mice once daily for either 31 (Groups 6 through 9) or 10 (Group 10) consecutive days.

On the $28^{th}$ day (Groups 1 through 4 and 6 through 9) or the $7^{th}$ day (Groups 5 and 10) of formulation administration, mice in Groups 1 through 10 were exposed to UVR (i.e., wavelengths in the UVB and UVA portions of the electromagnetic spectrum). The source of irradiation was a Berger Compact Arc high intensity solar simulator (Solar Light Company, Philadelphia, Pa.) with a WG320 Schott glass filter (1 mm) coupled to an Oriel light pipe. The radiant intensity of the source was monitored continuously with a PMA 2100 meter (Solar Light Company, Philadelphia, Pa.) or comparable device. On day 28 or 7, the interval between the formulation administration and the start of UVR exposure was less than 15 minutes for most mice and slightly more than 15 minutes for a small number of mice.

Checks for viability were made twice daily. Clinical observations were recorded at least weekly, including once before the first formulation administration and once immediately before UVR exposure. Clinical observations were also recorded at approximately 24, 48 and 72 hours after irradiation. Body weights were recorded once weekly during the administration period and at terminal sacrifice.

Sacrifice of Mice

All mice survived to schedule sacrifice. Scheduled sacrifice occurred after the final examination, approximately 72 hours after completion of the UVR exposures ($CO_2$ asphyxiation). Dorsal skin, including the UVR exposure sites, were removed and retained in neutral buffered 10% formalin for possible histopathological examination.

Calculated mean UVR dose values (MED) and standard deviations were determined for appropriate groups as follows. The lowest instrumental UVR dose to cause any cutaneous response at a site of exposure was determined for each mouse. The mean calculated UVR dose for each group for each observational time point was determined. If administration of the test article has no influence on the UVR dose required to elicit cutaneous responses, based on this method of calculation, a mean calculated UVR dose value equivalent to 1.0 MED would be expected at 48 hours after irradiation. A mean calculated UVR dose value greater than 1.0 would indicate a protective effect of the test article. For any mouse that had no skin reactions in any of the six UVR exposure sites, an imputed value of 2.8 was assigned for the purpose of calculation and the > symbol was included as a prefix to the group mean calculated UVR dose value. Additionally, ratios (clinical observations) and averages with standard deviations (body weights) were calculated.

Group means and standard deviations were calculated and tabulated for body weights and body weight changes.

Results

Skin reactions that occurred in the UVR exposure sites included erythema, edema and flaking and the severity of the skin reactions tended to be dependent on the UVR exposure dose.

There was an indication of a mild dosage-dependent protective effect against UVR-induced cutaneous inflammation in hairless mice orally administered Olivenol for 31 days and a moderate dosage-dependent protective effect in mice topically administered Olivenol for 31 days. In this type of study, it was anticipated that the mean calculated UVR dose value would be approximately equal to 1.0 at 48 hours after UVR exposure in naïve mice.

In mice orally administered Olivenol for 31 days (Groups 1 through 4), the mean calculated UVR dose values at 48 hours after UVR exposure were 1.2, 1.3, 1.4 and 1.5 in the 0 (Vehicle), 1, 10 and 100 mg/kg/day dosage groups, respectively. In mice topically administered Olivenol for 31 days (Groups 6 through 9), the mean calculated UVR dose values at 48 hours after UVR exposure were 1.5, 1.5, >1.9 and >2.2 in the 0 (Vehicle), 1, 10 and 100 mg/kg/day dosage groups, respectively. The > symbol was included as a prefix to the mean calculated UVR dose values in Groups 8 and 9 because no cutaneous reactions occurred in any of the UVR exposure sites for two mice in each of those groups. For those four mice an imputed value of 2.8 was assigned for the purpose of calculation.

At 72 hours after UVR exposure, the protective effect of the test article was less definitive. However, in mice topically administered 100 mg/kg/day Olivenol for 31 days (Group 9) the mean calculated UVR dose was 1.6 at 72 hours after UVR exposure, as compared with a value of 1.2 for the appropriate control group (Group 6).

The 1.5 mean calculated UVR dose value in Group 6 [0 (Vehicle), topical administration] at 48 hours after UVR exposure was unanticipated. Since the value was substantially greater than the anticipated value of approximately 1.0, the vehicle may have had some impact on cutaneous susceptibility to UVR exposure. However, there was a clear increase in the mean calculated UVR dose values in the mice topically administered 10 and 100 mg/kg/day Olivenol dosages for 31 days, as compared with mice topically administered 0 (Vehicle) mg/kg/day Olivenol.

There was no indication of a protective effect against UVR-induced cutaneous inflammation in hairless mice administered the 100 mg/kg/day Olivenol dosage for 10 days vial the oral (Group 5) or topical (Group 10) route, as compared with the appropriate control groups. In mice orally or topically administered the 100 mg/kg/day Olivenol dosage for 10 days, the mean calculated UVR dose values at 48 hours after UVR exposure were 1.0 and 1.3, respectively. These values were comparable to the values that occurred in the appropriate 0 (Vehicle) mg/kg/day dosage groups (i.e., Groups 1 and 6, respectively).

The skin reactions that occurred at 24 hours after UVR exposure were not considered useful in making a determination on the protective potential of the test article because these reactions tend to be less reproducible than those that occur later.

Two mice in each of Groups 1 and 3 developed urogenital ulcerations. One mouse in each of Groups 6 and 7 developed lump(s). These are common findings in male hairless mice and were not considered test article-related.

Necropsy revealed that all tissues appeared normal.

Body weight and body weight changes observed throughout the experimental protocol were unremarkable.

There was an indication of a mild dosage-dependent protective effect against UVR-induced cutaneous inflammation in male hairless mice orally administered Olivenol for 31 days and a moderate dosage-dependent protective effect in mice topically administered Olivenol for 31 days. The high Olivenol dosage, 100 mg/kg/day, afforded cutaneous protection via the oral and topical administration routes.

There was no indication of a protective effect against UVR-induced cutaneous inflammation in hairless mice administered the 100 mg/kg/day Olivenol dosage for 10 days via the oral or topical route.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Further, the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but puts them forth only as possible explanations.

The invention claimed is:

1. A method of producing a hydroxytyrosol-rich composition, comprising
    (a) producing vegetation water from olives, wherein said vegetation water comprises oleuropein;
    (b) adding acid to the vegetation water thereby producing acidified vegetation water; and
    (c) incubating the acidified vegetation water for a period until (i) at least 50% of oleuropein originally present in the vegetation water has been converted to hydroxytyrosol, and (ii) the vegetation water has a weight ratio of hydroxytyrosol to tyrosol of between about 3:1 and about 50:1.

2. The method of claim 1, wherein said incubating is carried out until at least 75% of oleuropein originally present in the vegetation water has been converted to hydroxytyrosol.

3. The method of claim 1, wherein said incubating is carried out for a period of at least 2 months, and until at least 90% of oleuropein originally present in the vegetation water has been converted to hydroxytyrosol.

4. The method of claim 1, wherein said producing step comprises producing vegetation water from the meat or pulp of depitted olives.

5. The method of claim 4, wherein the incubating is carried out until the vegetation water has a weight ratio of hydroxytyrosol to oleuropein of between about 1:1 and about 200:1.

6. The method of claim 5, wherein the incubating is carried out until the vegetation water has a weight ratio of hydroxytyrosol to oleuropein of between about 4:1 and about 200:1.

7. The method of claim 6, wherein, the incubating is carried out until the vegetation water has a weight ratio of hydroxytyrosol to oleuropein of between about 10:1 and about 100:1.

8. The method of claim 1, wherein the incubating is carried out until the vegetation water has a weight ratio of hydroxytyrosol to tyrosol of between about 5:1 to about 30:1.

9. The method of claim 1, which further comprises fractionating the incubated vegetation water to separate hydroxytyrosol from other components.

10. The method of claim 1, which further comprises extracting the incubated vegetation water with an organic solvent to produce a fraction enriched by 20% or more in hydroxytyrosol.

11. The method of claim 10, which further comprises the purification of hydroxytyrosol by chromatography.

12. The method of claim 10 wherein the organic solvent is ethyl acetate.

13. The method of claim 1, wherein said acid is added in an amount effective to produce a pH between about 1 and about 5.

14. The method of claim 1, wherein said acid is added in an amount effective to produce a pH between about 2 and about 4.

15. The method of claim 1, wherein said acid is citric acid.

16. The method of claim 1, wherein the concentration of hydroxytyrosol in the vegetation water from (c) ranges from 4 grams per liter to 15 grams per liter.

17. The method of claim 1, wherein said incubating is for a period of at least two months.

18. The method of claim 1 wherein said incubating is for a period of approximately twelve months.

* * * * *